United States Patent [19]

Hutton et al.

[11] 4,130,573
[45] Dec. 19, 1978

[54] PROCESS FOR MAKING ORGANOTIN DIHALIDES AND TRIHALIDES

[75] Inventors: Ronald E. Hutton, Southport; Joseph W. Burley, Wallasey, both of England

[73] Assignee: Akzo N.V., Arnhem, Netherlands

[21] Appl. No.: 791,775

[22] Filed: Apr. 28, 1977

Related U.S. Application Data

[62] Division of Ser. No. 660,631, Feb. 23, 1976, Pat. No. 4,080,363.

[30] Foreign Application Priority Data

Mar. 17, 1975 [NL] Netherlands ................. 7503116

[51] Int. Cl.² ........................................ C07F 7/22
[52] U.S. Cl. ........................ 260/429.7; 260/45.75 E
[58] Field of Search ............................. 260/429.7

[56] References Cited

U.S. PATENT DOCUMENTS

| | | | |
|---|---|---|---|
| 3,161,664 | 12/1964 | Depree | 260/429.7 |
| 3,398,169 | 8/1968 | Neumann et al. | 260/429.7 |
| 3,403,169 | 9/1968 | Rudner et al. | 260/429.7 |
| 3,412,122 | 11/1968 | Considine | 260/429.7 |
| 3,440,255 | 4/1969 | Matsuda et al. | 260/429.7 |

OTHER PUBLICATIONS

Matsuda et al., J. Organometallic Chem. V18, 95-104 (1969).
Omae et al., J. Organometallic Chem. V24, 663-666 (1970).
Matsudo et al., J. Organometallic Chem. V25, 101-109 (1970).

Primary Examiner—Helen M. S. Sneed
Attorney, Agent, or Firm—Stevens, Davis, Miller & Mosher

[57] ABSTRACT

An organotin dihalide having the formula

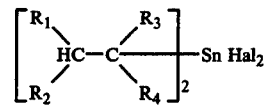

or a mixture of the dihalide and an organotin trihalide is prepared by reacting metallic tin with an olefin having the formula

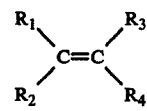

wherein $R_1$, $R_2$, and $R_4$ are hydrogen or a hydrocarbon radical and at least one of $R_1$ or $R_2$ contains an oxygen-containing group with a carbonyl group adjacent to the olefinic double bond and Hal is a halogen. The organotin dihalide or mixture thereof with a trihalide is reacted with an acid or mercaptan to produce a stabilizer for polyvinyl chloride polymers and the like.

5 Claims, No Drawings

PROCESS FOR MAKING ORGANOTIN DIHALIDES AND TRIHALIDES

This is a Division of application Ser. No. 660,631 filed Feb 23, 1976, now U.S. Pat. No. 4,080,363.

This invention relates to a process for the preparation of organotin halides starting from metallic tin. The invention also relates to compounds derived from these organotin dihalides, which compounds are suitable to be used as stabilizers for polymers such as polyvinyl chloride. Organotin halides are important intermediate products in the preparation of organotin stabilizers for polymers.

Commercial methods for the preparation or organotin halides often make use of the Grignard reaction, the aluminum alkyl compounds, or the Würtz route, tin chloride being converted into tetraalkyl tin which is subsequently converted into an alkyl tin halide. These methods, however, are relatively costly and moreover they present some hazard to the people conducting them.

Another known method which is less dangerous and less elaborate starts with metallic tin which is directly reacted with an alkyl halide to form an alkyl tin halide. The lastmentioned direct route is described in, for instance, the U.S. Pat. No. 3,745,183. This known direct route, however, is unattractive from a commercial point of view because it calls for the use of catalysts at a relatively high temperature and leads to considerable losses of tin as a result of the formation of by-products.

It is therefore an object of this invention to provide a process for making an organotin dihalide which is devoid of the foregoing disadvantages. Another object of the invention is to provide a process for making an organotin dihalide which does not require high temperatures and catalysts. A more specific object of the invention is to provide a process for making an organotin dihalide at normal temperatures and pressures without a catalyst and without the formation of significant amounts of undesirable by-products.

The foregoing objects and others are accomplished in accordance with this invention by providing a process wherein metallic tin is reacted with a hydrogen halide and an olefin having the formula

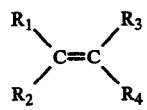

wherein $R_1$, $R_2$, $R_3$ and $R_4$ represents hydrogen or a hydrocarbon group, provided that of $R_1$ and $R_2$ at least one is an oxygen-containing group with a carbonyl group adjacent to the olefinic double bond to form an organotin dihalide having the formula

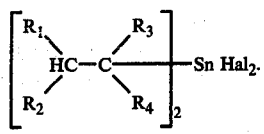

The reaction between metallic tin, a hydrogen halide and an olefin of the above formula activated by one or more carbonyl groups gives a high yield, calculated on tin, even under normal conditions of temperatures and pressure and without the use of a catalyst.

It is preferred to use as the hydrogen halide the relatively inexpensive hydrogen chloride but hydrogen bromide or other suitable hydrogen halide may be used.

Any suitable olefin having an activating carbonyl radical may be used, such as, for example, an olefin containing an acid group, an ester group, an aldehyde group or a keto group. As examples of suitable olefins may be mentioned:

| | |
|---|---|
| acrylic acid | acryloyl chloride |
| methyl acrylate | 1,1 bis(carboxy ethyl) propylene |
| methyl crotonate | methyl vinyl ketone |
| methyl 2-cyclohexyl acrylate | mesithyl oxide, and |
| cinnamic acid | methyl styryl ketone. |
| cinnamic methyl ester | |

Accordingly, the process of this invention is preferably performed using an olefin of the above formula wherein at least one of $R_1$ and $R_2$ is an oxygen-containing group having the formula

wherein $R_5$ is hydrogen, hydroxyl, halogen, amino or alkyl, substituted alkyl or alkoxy containing 1–18 carbon atoms.

Optionally, the reaction may be carried out in a solvent. As examples of suitable organic solvents may be mentioned: ethers, alcohols, esters and chlorinated or non-chlorinated hydrocarbons. An excess of the olefin may be used as the solvent.

The metallic tin may be used in any form. It is in principal preferred to use powdered tin because of its increased reaction speed as a result of the large available tin surface. Direct use may, however, also be made of commercially available granulated tin. In the later case a moderate increase in reaction temperature is advisable in order to increase the reaction speed.

The process provided by the invention normally leads to the formation of a functionally substituted organotin dihalide having the general formula $(R)_2SnHal_2$, where R represents the afore-defined group:

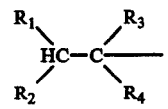

These novel compounds now form the starting product for the preparation by techniques known in themselves of exceptionally good, novel organotin stabilizers for polyvinyl chloride and other polymers, the halogen atoms being replaced with the usual organic residues such as acid, thio ester and thio alkyl groups.

From the alkyl tin stabilizer art it is known that a mixture of dialkyl tin and monoalkyl tin stabilizers has a synergistic effect.

From previous investigations carried out by applicant it appears that tin dihalide, hydrogen halide and a carbonyl activated olefin of the above formula react with each other to from an organotin trihalide having the general formula $RSnHal_3$.

It now been found that the process according to the invention can be so controlled that part of the metallic tin first converts into tin dihalide, which subsequently reacts to form organotin trihalide.

It this way now it is possible for a metallic tin to be directly processed into a mixture of $(R)_2SnHal_2$ and $RSnHal_3$, which mixture can subsequently be directly converted into the desired synergistic stabilizer mixture.

As will be apparent from the following examples, the amount of trihalide in the organotin halide can be varied between wide limits, for instance from 0-95% by weight. If a mixture is to be obtained, the amount of trihalide will usually be in the range of about 5-60% by weight.

For the simultaneous formation is the reaction product of an arbitrary amount of trihalide it is essential that the competing reactions between tin and hydrogen halide on the one hand and between these substances and the activated olefin on the other be influenced in favor of the former reaction.

The formation of the trihalide may therefore be promoted especially by changing the proportions of the reactants, the order in which and/or the speed at which the reactants are added, the available tin surface and, to a lesser extent, the temperature.

Thus for instant the use of an excess of olefin, a slow addition of the hydrogen halide and a reduction of the available tin surface will tend to lead to an exclusive formation of the dihalide $(R)_2SnHal_2$.

Changing the reaction conditions in reverse order will lead to increased formation of the trihalide $RSnHal_3$.

Organotin dihalides $(R)_2SnHal_2$ mixed, it desired, with $RSnHal_3$, and reacted with acids or mercaptans in the usual manner will result in the formation of excellent stabilizers haivng the general formula $(R)_2SnX_2$ which may be mixed with $RSnX_3$. These organotin salts with acid residue X are preferably formed by reaction with alkyl thiocarboxylic esters, alkyl thiols, monocarboxylic acids and partial esters of polycarboxylic acids.

As specific examples of good stabilizers derived from the present organotin dihalides may be mentioned:

Alkyl thiocarboxylates $(MeOCOCH_2CH_2)_2Sn(S(CH_2)_nCOOC_8H_{17})_2$
$(BuOCOCH_2CH_2)_2Sn(S(CH_2)_nCOOC_8H_{17})_2$
$(C_{18}H_{37}OCOCH_2CH_2)_2Sn(S(CH_2)_nCOOC_8H_{17})_2$
$(BuOCOCH_2CH_2)_2Sn(S(CH_2)_nCOOBu)_2$
where n=1 (thioacetate) or 2 (thiopropionate).

Alkyl mercaptides $(MeOCOCH_2CH_2)_2Sn(SC_{12}H_{25})_2$
$(BuOCOCH_2CH_2)_2Sn(SC_{18}H_{37})_2$
$(C_{12}H_{25}OCOCH_2CH_2)_2Sn(SC_{12}H_{25})_2$

Carboxylates $(MeOCOCH_2CH_2)_2Sn(OCOC_{11}H_{23})_2$
$(BuOCOCH_2CH_2)_2Sn(OCOC_{17}H_{35})_2$

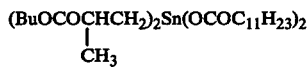

Partial esters $(MeOCOCH_2CH_2)_2Sn(OCOCH = CHCOO\ Bu)_2$
$(BuOCOCH_2CH_2)_2Sn(OCOCH = Me)_2$
Me in the above formula is methyl and Bu is butyl.

The organotin stabilizers according to the invention will generally lead to a better heat resistance of polymers, more particularly PVC, than the traditional butyl tin stabilizers.

In the case of sulphur-containing stabilizers the odor is found to be considerably improved.

Particularly in the foodstuffs branch (packaging film and the like) the toxicity of the stablilizer is of great importance.

It has been found that in this respect various stabilizers according to the invention are considerably more favorable than the traditional butyl tin stabilizers.

Thus the L.D. 50-value (i.e., the dose at which 50% of the laboratory animals die) of the traditional stabilizer $(C_4H_9)_2Sn(SCH_2COOC_8H_{17})_2$ for rats is about 500 mg per kg of body weight. For the compound $(CH_3OCOCH_2CH_2)_2Sn(SCH_2COOC_8H_{17})_2$, however, this value is of the order of magnitude of 12,000 mg/kg.

The following examples are given for the purpose of illustrating the present invention.

Examples I–XII describe the preparation of the present organotin dihalides with or without simultaneous formation of trihalides. Examples XIII–XVI are concerned with the preparation of stabilizers from these halides.

Example XVII describes a comparative test with these stabilizers incorporated in PVC.

EXAMPLE I

Into a 500-ml three-necked flask placed in a cooling bath and equipped with a stirrer, a thermometer, a condenser and a gas inlet tube, 60 g of powdered tin, 87.4 g of methyl acrylate and as solvent 140 ml of diethyl ether were charged.

A total of 87 grams of dry hydrogen chloride were added to the flask over a period of about 3 hours at a temperature of 20° C. with stirring. Subsequently, the ether was evaporated off and the residue extracted with 300 ml of hot chloroform. About 0.5 g of unreacted tin with traces of stannous chloride were left.

From the chloroform extract the chloroform was removed at 100° C. and 4 mm Hg, after which there remained 177.2 g of a whitish solid substance.

Upon analysis (nuclear spin resonance spectroscopy) this whitish substance was found to be a mixture of organotin di- and trihalides, namely $Cl_2Sn(CH_2CH_2COOCH_3)_2$ and 27% by weight of $Cl_3SnCH_2CH_2COOCH_3$.

The yield was quantitative based on the converted tin. After the mixture had been washed with diethyl ether, in which the trichloride is substantially soluble, there remained a white, crystalline substance which upon repeated analysis (infrared and nuclear spin resonance spectroscopy and elementary analysis) was found to be pure $Cl_2Sn(CH_2CH_2COOCH_3)_2$ having a melting point of 132° C.

EXAMPLE II

By the method used in Example I, 60 g of powdered tin, 95.7 g of methyl acrylate and 110 ml of diethyl ether were charged into the flask. And over a period of about 14 hours and at 20° C. a total of 42 g of dry hydrogen chloride gas were passed into the mixture.

As in Example I, the solvent was removed and the residue extracted, after which there remained 3.7 g of non-converted tin; and 167.2 grams of white solid substance were recovered from the extract.

The substance was found to be a mixture of $Cl_2Sn(CH_2CH_2COOH_3)_2$ and 3.5% by weight of $Cl_3SnCH_2CH_2COOCH_3$.

The yield was 98%, calculated on the amount of tin used.

EXAMPLE III

By the method of Example I, 60 g of powdered tin, 37.1 g of methyl acrylate and 140 ml of hexane were charged into the flask and over a period of 12½ hours, 46 g of dry hydrogen chloride gas were introduced. The reaction mixture was filtered, washed with 100 ml of hexane and extracted with hot chloroform, after which there remained 1.5 g of non-converted tin and the extract yielded 173 g of solid matter.

Upon analysis this solid matter was found to be a mixture of $Cl_2Sn(CH_2CH_2COOCH_3)_2$ and 15.9% by weight of $Cl_3SnCH_2COOCH_3$. The yield was 99%, calculated on converted tin.

EXAMPLE IV

Into the flask of Example I, there were introduced 60 1 g of powdered tin and 95.7 g of methyl acrylate. Over a period of 45 minutes in all, 115 g of hydrochloric acid (35.4%) were added with stirring, after which the stirring was continued for 4 hours. Subsequently, the reaction mixture was filtered off, washed with water and extracted with chloroform. There remained 14.9 g of non-converted tin and, from the extract there were obtained 103.5 g of solid substance, which upon analysis was found to be pure $Cl_2Sn(CH_2CH_2COOCH_3)_2$, the remainder being contained as tin chloride in the wash water.

EXAMPLE V

By the method of Example I, 60 g of powdered tin and 174.2 g of methyl acrylate (also servng as a solvent) were brought into the flask. Next, over a period of 15 hours, in all 40 g of dry hydrogen chloride gas were introduced. The reaction mixture was filtered and washed with 20 g of methyl acrylate.

Upon extraction with chloroform 5.0 g of non-converted tin were left and the extract gave 141.2 g of crystalline product of pure $Cl_2Sn(CH_2CH_2COOCH_3)_2$ in 84.6% yield, calculated on converted tin. The filtrate was still found to contain 17.3 g of said product, the final yield being 95%.

EXAMPLE VI

In accordance with the procedure used in Example I, 60 g of powdered tin, 95.7 g of methyl acrylate and 140 ml of diethyl ether were charged into the flask. Subsequently, over a period of 10¾ hours in all, 110 g of dry hydrogen bromide gas were introduced.

After the solvent had been removed, the residue was extracted with 300 ml of hot chloroform and 9.5 g of non-converted tin were left.

Evaporation of the extract gave 196.0 g of solid substance, which was analyzed as a mixture of $Br_2Sn(CH_2CH_2COOCH_3)_2$ having a melting point of 137° C. and 19.7% by weight of $Br_3SnCH_2CH_2COOCH_3$. The yield was quantitative, calculated on converted tin.

EXAMPLE VII

Into the flask of Example I, there were brought 60 g of powdered tin, 99.2 g of mesityl oxide ad 140 ml of diethyl ether.

Subsequently, over a period of 10½ hours, there were introduced 70 g of dry hydrogen chloride gas.

After filtration and washing with 150 ml of ice-cold ether, the residue was extracted with 300 ml of chloroform. No tin was left and the extract yielded 84.6 g of light brown crystalline substance, which was pure $Cl_2Sn(CH_3)_2CH_2COCH_3)_2$ having a melting point of 158° C.

The yield, calculated on converted tin, was 43%.

After evaporation the ether filtrate still gave 89.5 g of dark brown product, which was found to contain about 40% by weight of $Cl_2Sn(CH_3)_2CH_2COCH_3)_2$ and 40% by weight of $Cl_3Sn(CH_3)_2CH_2COCH_3$.

So the final total yield of organotin compounds was about 80%.

EXAMPLE VIII

Into the flask of Example I, there were brough 60 g of powdered tin, 78.0 g of methyl vinyl ketone and 140 ml of diethyl ether. Subsequently, over a period of 14 hours, 54 g of dry hydrogen chloride gas were introduced. The reaction mixture was filtered to remove traces of non-converted tin (about 0.1 g) and next evaporated at 100° C. and 4 mm Hg, after which 162.4 g of a dark brown solid substance was left.

Upon analysis this substance was found to contain about 40% by weight of $Cl_2Sn(CH_2CH_2COCH_3)_2$ and 40% by weight of $Cl_3SnCH_2CH_2COCH_3$.

Tht total yield of organotin compounds was about 80%, calculated on converted tin.

EXAMPLE IX

Into the flask of Example I, there were charged 60 g of powdered tin, 91.5 g of acryloyl chloride and 140 ml of diethyl ether. Over a period of 19½ hours, a total of 60 g of dry hydrogen chloride gas were introduced. Filtration resulted in removing 24 g of non-converted tin from the reaction mixture, which was subsequently evaporated. The residue was extracted with 300 ml of hot chloroform, after which the extract was boiled down to 103 g of a brown solid substance. Upon analysis this substance was found mainly to contain $Cl_3SnCH_2CH_2COCl$ in addition to some $Cl_2Sn(CH_2CH_2COCl)_2$. Accurate determination of the yield was difficult because of the presence of organic material.

EXAMPLE X

Into the flask of Example I, there were brought 60 g of powdered tin, 129.6 g of n=butyl acrylate and 140 ml of diethyl ether. Over a period of 20 hours, 54 g of dry hydrogen chloride gas were introduced. Filtration of the reaction mixture resulted in removing 0.2 g of non-converted tin, after which the filtrate was boiled down to 224 g of a clear, colorless liquid which upon analysis was found to consist mainly of $Cl_2Sn(CH_2CH_2COOC_4H_9)_2$ in addition to a small amount of $Cl_3SNCH_2CH_2COOC_4H_9$.

The total yield was about 97%, calculated on converted tin. The reaction produce being a liquid here, the method used in this example is excellently suitable for continuous process operation.

EXAMPLE XI

Into the flask of Example I, there were brought 60 g of powdered tin, 101.2 g of methyl methacrylate and 140 ml of diethyl ether. Subsequently, over a period of 22 hours, 44 g of dry hydrogen chloride gas were introduced. The reaction mixture was evaporated and the residue extracted with 300 ml of hot chloroform. In this way 33.3 g of non-converted tin were left and the extract finally yielded 67.3 g of crystalline material, which upon analysis was found to consist of $Cl_2Sn(CH_2CHMeCOOCH_3)_2$ having a melting point of 111° C. and 57.5% by weight of $Cl_3SnCHCH_3COOCH_3$.

The total yield was 84%, calculated on converted tin.

EXAMPLE XII

The flask of Example I was equipped with a heating jacket and filled with 60 g of granulated tin and 129.6 g of n-butyl acrylate. The contents of the flask were then heated to 120° C., after which over a period of 12 hours, 78 g of dry hydrogen chloride gas were introduced. The reaction mixture was filtered to separate the non-converted tin (9.8 g) and the filtrate was evaporated to remove the remaining butyl acrylate and hydrochlorinated acrylate as by-product. There remained 179.8 g of a clear, practically colorless liquid, which upon analysis was found mainly to consist of $Cl_2Sn(CH_2CH_2COOC_4H_9)_2$. The yield was 95%, calculated on converted tin. The product was slightly contaminated with poly-butyl acrylate.

EXAMPLE XIII

Into a 600-ml beaker provided with a stirrer, a thermometer and a heating plate there were brought 54.6 g of $Cl_2Sn(CH_2CH_2COOCH_3)_2$ (isolated as in Example I), 64.3 g of isooctyl thioglycolate and as solvent 200 ml of tetrahydrofuran.

To the mixture were added, with stirring, 26.6 g of anhydrous sodium bicarbonate, followed by heating for 2 hours at 50°-60° C. The resulting sodium chloride was filtered off and the filtrate boiled down to 104.8 g of a colorless liquid. The hot liquid was again filtered and characterized by analysis as $(CH_3OCOCH_2CH_2)_2Sn(SCH_2COOC_8H_{17})_2$.

By the above synthesis it is also possible for a mixture of organotin di- and trihalides to be formed into a mixture of the corresponding thioglycolate tin compounds.

EXAMPLE XIV

Into a three-necked flask of the type used in Example I, there were brought 64.5 g of lauric acid and 12 g of sodium hydroxide dissolved in 250 ml of water. The temperature was increased to 70°-80° C., followed by the addition of 54.6 g of $Cl_2Sn(CH_2CH_2COOCH_3)_2$, and the increased temperature was maintained for 1 hour. Subsequently, 150 ml of toluene were added and stirring was continued for 5 more minutes.

The resulting toluene layer was separated and boiled down to 102 g of a light yellow liquid containing $(CH_3OCOCH_2CH_2)_2Sn(OOCC_{11}H_{23})_2$.

By the same procedure as used above, a mixture of organotin di- and trihalidees can be formed into a mixture of corresponding laurate tin compounds.

EXAMPLE XV

Into a 600-ml beaker there were charged 72.7 g of $Cl_2Sn(CH_2CH_2COOCH_3)_2$, 80.8 g of lauryl thiol and as solvent 250 ml of tetrahydrofuran. After addition, with stirring, of 42.4 g of anhydrous sodium carbonate the mixture was heated for 1 hour at 60° C. Subsequently, the sodium chloride was filtered off and the filtrate boiled down to 137 g of a colorless liquid which upon analysis was found to be composed as follows: $(CH_3OCOCH_2CH_2)_2Sn(S-C_{12}H_{25})_2$.

In the same way, mixtures of di- and tri thiolauryl tin compounds can be obtained.

EXAMPLE XVI

Into a 600-ml beaker there were charged 72.7 g of $Cl_2Sn(CH_2CH_2COOCH_3)_2$, 68.8 g of monobutyl maleate and as solvent 250 ml of tetrahydrofuran. After addition of 33.6 g of anhydrous sodium bicarbonate, the temperature was kept at 60° C. for 1 hour. The sodium chloride was filtered off and the filtrate boiled down to 124 g of a colorless liquid containing $(CH_3OCOCH_2CH_2)_2 Sn(OCOCH=CHCOOC_4H_9)_2$.

In the same way the corresponding organotin di- and trihalides may be formed into mixtures of di- and tri-maleate tin compounds.

EXAMPLE XVII

Of the organotin compounds having the general formula $(CH_3OCOCH_2CH_2)_2SnX_2$ obtained in the Examples XIII through XVI the stabilizing effect was tested in polyvinyl chloride and compared with that of the known dibutyl stabilizers $(C_4H_9)_2SnX_2$.

In each case there were added 2% by weight of stabilizer, calculated on (plasticized) PVC and the heat resistance was determined on the basis of discoloration with time at a temperature of 185° C.

A test was also carried out on PVC bottles containing 1% by weight of a mixture of the stabilizer according to Example XIII and 10% by weight of the corresponding $RSnX_3$ compounds and on bottles containing 1% by weight of only the last-mentioned compound.

The results are summarized in the following table.

Table

| | Heat resistance of stabilized PVC at 185° C. | | | | | | | | | |
|---|---|---|---|---|---|---|---|---|---|---|
| | $(C_4H_9)_2SnX_2$ where X | | | | $(CH_3OCOCH_2CH_2)_2SnX_2$ where X | | | | $CH_3OCOCH_2CH_2SnX_3$ wahere X | |
| stab. min. | IOTG | L | LT | MBM | IOTG | L | LT | MBM | IOTG (with 10% $X_3$) | IOTG |
| 0 | c | c | v.l. | c | c | c | c | v.l.y. | c | c |
| 50 | l.y. | o | y | b | c | v.l.y. | c | o | c | l.y. |
| 70 | y | d.o. | y | | v.l.y. | b | y | b | c | b |

Table-continued

| | (C₄H₉)₂SnX₂ where X | | | | (CH₃OCOCH₂CH₂)₂SnX₂ where X | | | | CH₃OCOCH₂CH₂SnX₃ where X | |
|---|---|---|---|---|---|---|---|---|---|---|
| stab. min. | IOTG | L | LT | MBM | IOTG | L | LT | MBM | IOTG (with 10% X₃) | IOTG |
| 90 | b | b | b | b | b | | | b | b | |

IOTG = iso octyl thioglycolate (Example XIII)
L = laurate (Example XIV)
LT = lauryl thio- (Example XV)
MBM = monobutylmaleate- (Example XVI)
c = colorless
y = yellow
o = orange
b = black
l. = light
v.l. = very light
d. = dark The table shows that the stabilizers according to the invention lead to improved stability. This is particularly evident from the considerably improved "early color", i.e., little or no change in color in the first heating period.

Although the invention is described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of organotin halides which comprises reacting metallic tin with a hydrogen halide and an olefin having the formula $$\begin{array}{c} R_1 \\ \phantom{R}\diagdown \\ R_2 \end{array} C=C \begin{array}{c} R_3 \\ \diagup\phantom{R} \\ R_4 \end{array}$$

wherein $R_1$, $R_2$, $R_3$ and $R_4$ represent hydrogen or a hydrocarbon group, provided that of $R_1$ and $R_2$ at least one is an oxygen-containing group with a carbonyl group adjacent to the olefinic double bond to form an organotin dihalide having the formula

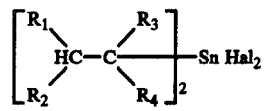

2. A process according to claim 1 wherein at least one $R_1$ or $R_2$ is an oxygen-containing group having the formula

wherein $R_5$ is hydrogen, hydroxyl, halogen, amino or alkyl, or alkoxy containing 1–18 carbon atoms.

3. The process of claim 1 wherein an organotin trihalide having the formula

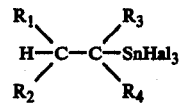

is formed simultaneously with the organotin dihalide.

4. The process of claim 3 wherein a mixture of organotin halides containing 5–60% by weight of organotin trihalide is formed.

5. The process of claim 1 wherein the olefin is selected from the group consisting of acrylic acid, acrylate esters, acrylate amides, vinyl alkyl ketones and acryloyl halides.

* * * * *